(12) United States Patent
Aoki

(10) Patent No.: US 8,877,953 B2
(45) Date of Patent: Nov. 4, 2014

(54) METHOD FOR PRODUCING SANSHOOL

(71) Applicant: Tsumura & Co., Tokyo (JP)

(72) Inventor: Katsuyuki Aoki, Ibaraki (JP)

(73) Assignee: Tsumura & Co., Tokyo (JP)

( * ) Notice: Subject to any disclaimer, the term of this patent is extended or adjusted under 35 U.S.C. 154(b) by 0 days.

(21) Appl. No.: 13/851,698

(22) Filed: Mar. 27, 2013

(65) Prior Publication Data
US 2013/0261327 A1 Oct. 3, 2013

(30) Foreign Application Priority Data

Mar. 28, 2012 (JP) ................. 2012-074423

(51) Int. Cl.
*C07F 15/02* (2006.01)
*C07C 233/09* (2006.01)
*C07C 231/12* (2006.01)

(52) U.S. Cl.
CPC ............. *C07C 231/12* (2013.01); *C07C 233/09* (2013.01); *C07F 15/02* (2013.01)
USPC ......................................... 556/141; 564/204

(58) Field of Classification Search
USPC .......................................... 556/141; 564/204
See application file for complete search history.

(56) References Cited

U.S. PATENT DOCUMENTS

2013/0245303 A1\* 9/2013 Aoki ............................ 556/141

OTHER PUBLICATIONS

Katsuyuki et al., "Application of iron carbonyl complexation to the selective total synthesis of sanshools", Tetrahedron Letters, vol. 53, No. 45 (Nov. 1, 2012), pp. 6000-6003.
European Search Report dated Jul. 25, 2013 in counterpart application 13160811.9.
Leslie Crombie et al., "Synthesis of Natural Polyene Isobutylamides. Stereochemistry of the Wittig Reactions" Tetrahedron Letters, 1985, pp. 2481-2484, vol. 26, No. 20.
Philip E. Sonnet, "Synthesis of the N-Isobutylamide of all-trans-2,6,8,10-Dodecatetraenoic Acid", The Journal of Organic Chemistry, Apr. 1969, vol. 34, No. 4.

\* cited by examiner

*Primary Examiner* — Porfirio Nazario Gonzalez
(74) *Attorney, Agent, or Firm* — Sughrue Mion, PLLC

(57) ABSTRACT

Provided are a method for producing a sanshool, which can produce a sanshool in a short process and with high stereoselectivity, as well as a novel diene iron complex compound that is a stable intermediate useful for the production method. The diene iron complex compound is represented by the following general formula (I):

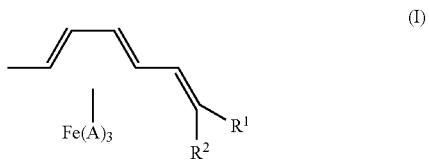

(I)

(in which A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^1$ and $R^2$ represents a hydrogen atom and the other one thereof represents a structure represented by the following formula (II)):

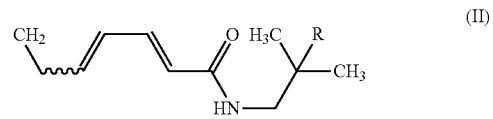

(II)

(in which R represents a hydrogen atom, a hydroxyl group, or a methyl group).

10 Claims, No Drawings

METHOD FOR PRODUCING SANSHOOL

TECHNICAL FIELD

The present invention relates to a method for producing a sanshool and to a diene iron complex compound that is an intermediate useful for the production method. In particular, the invention relates to a method for producing a sanshool, which can produce a sanshool in a short process and with high stereoselectivity, as well as to a novel diene iron complex compound that is an intermediate useful for the production method.

BACKGROUND ART

Sanshools are a main ingredient of a crude drug, "Zanthoxylum Fruit". In recent years, gamma-sanshool has been reported to have effects such as the activation of TRPV1 and is now in the spotlight of the medicinal chemical field.

The sanshools including gamma-sanshool and delta-sanshool have an unstable structure due to a triene moiety. Therefore, it has been difficult to constantly produce and supply sanshool as a pure substance. Conventionally, from an extract of sanshool as a raw material, sanshool has been isolated and purified by silica gel and ODS column chromatography.

Total syntheses of gamma-sanshool and delta-sanshool have not been reported in the past, but a total synthesis of alpha-sanshool as an analogue of the sanshools has been reported (see Non-Patent Documents 1 and 2). Methods described in the Non-Patent Documents 1 and 2 are both those for forming a triene moiety by a Wittig reaction.

RELATED ART DOCUMENTS

Non-Patent Documents

Non-Patent Document 1: Sonnet P. E., J. Org. Chem., 1969, 34, 1147-1149.
Non-Patent Document 2: Crombie L., Fisher D., Tetrahedron Lett., 1985, 26, 2481-2484.

SUMMARY OF THE INVENTION

Problems to be Solved by the Invention

However, the methods described in Non-Patent Documents 1 and 2 have showed low yield and low E/Z selectivity and thus can hardly be said to be practical synthesis methods.

Therefore, it is an object of the present invention to provide a method for producing a sanshool, which can produce a sanshool in a short process and with high stereoselectivity, as well as a novel diene iron complex compound that is a stable intermediate useful for the production method.

Means for Solving the Problems

The present inventors conducted extensive and intensive research to solve the above problems and found that the problems can be solved by using a specific novel diene iron complex compound, thereby completing the present invention.

A diene iron complex compound according to the present invention and a method for producing a sanshool according to the present invention are as described in the following [1] to [10].

[1] A diene iron complex compound represented by the following general formula (I):

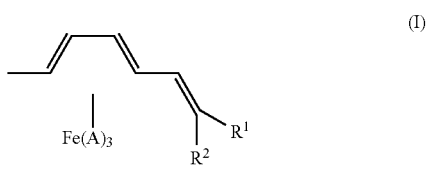

(in which A represents CO, $P(R^4)_3$, CN, NO, $SO(R^4)_3$, or $N(R^4)_2$; $R^4$ represents a straight chain or branched chain alkyl group having 1 to 4 carbon atoms or an aryl group having 6 to 12 carbon atoms; and one of $R^1$ and $R^2$ represents a hydrogen atom and the other one thereof represents a structure represented by the following formula (II)):

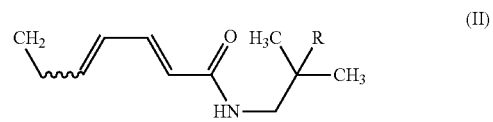

(in which R represents a hydrogen atom, a hydroxyl group, or a methyl group).

[2] A method for producing a sanshool, including a step of reacting a diene iron complex compound represented by the following general formula (I):

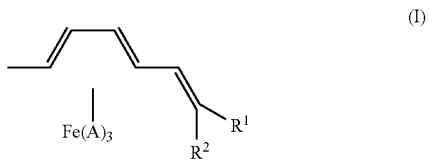

(in which A represents CO, $P(R^4)_3$, CN, NO, $SO(R^4)_3$, or $N(R^4)_2$; $R^4$ represents a straight chain or branched chain alkyl group having 1 to 4 carbon atoms or an aryl group having 6 to 12 carbon atoms; and one of $R^1$ and $R^2$ represents a hydrogen atom and the other one thereof represents a structure represented by the following formula (II)):

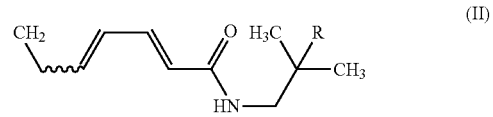

(in which R represents a hydrogen atom, a hydroxyl group, or a methyl group) with a deprotecting agent.

[3] The method for producing a sanshool according to [2], in which the deprotecting agent is selected from the group consisting of cerium (IV) compounds, trimethylamine N-oxide, pyridine N-oxide, iron (III) chloride, copper (II) chloride, dichlorodicyano benzoquinone, and hydrogen peroxide.

[4] The method for producing a sanshool according to [2] or [3], further including:

a step of reducing a diene iron complex compound represented by the following general formula (III):

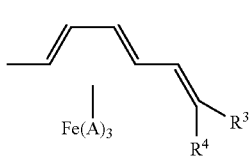
(III)

(in which A represents CO, P(R^A)_3, CN, NO, SO(R^A)_3, or N(R^A)_2; R^A represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group) to an aldehyde compound; and a step of reacting the obtained aldehyde compound with (E)-N-isobutyl-diethylphosphonocrotonic acid amide, (E)-N-(2-methyl-2-hydroxy-propyl)-diethylphosphonocrotonic acid amide, or (E)-N-(2,2-dimethyl-propyl)-diethylphosphonocrotonic acid amide to obtain the diene iron complex compound represented by the general formula (I).

[5] The method for producing a sanshool according to [4], in which lithium hydroxide is used as a base in the step of reacting the aldehyde compound with (E)-N-isobutyl-diethylphosphonocrotonic acid amide, (E)-N-(2-methyl-2-hydroxy-propyl)-diethylphosphonocrotonic acid amide, or (E)-N-(2,2-dimethyl-propyl)-diethylphosphonocrotonic acid amide.

[6] The method for producing a sanshool according to [2] or [3], further including:

a step of reducing a diene iron complex compound represented by the following general formula (III)

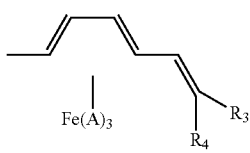
(III)

(in which A represents CO, P(R^A)_3, CN, NO, SO(R^A)_3, or N(R^A)_2; R^A represents a straight chain or branched chain alkyl group having 1 to 4 carbon atoms or an aryl group having 6 to 12 carbon atoms; and one of $R_3$ and $R_4$ represents a hydrogen atom and the other one thereof represents a 2-cyanoethyl group) to an aldehyde compound;

a step of reacting the obtained aldehyde compound with triethyl 4-phosphonocrotonate to obtain a diene iron complex compound represented by the following general formula (IV):

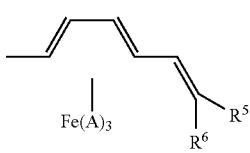
(IV)

(in which A represents CO, P(R^A)_3, CN, NO, SO(R^A)_3, or N(R^A)_2; R^A represents a straight chain or branched chain alkyl group having 1 to 4 carbon atoms or an aryl group having 6 to 12 carbon atoms; and one of $R^5$ and $R^6$ represents a hydrogen atom and the other one thereof represents a structure represented by the following formula (V))

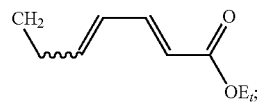
(V)

and a step of hydrolyzing the obtained diene iron complex compound represented by the general formula (IV) and then reacting the resulting compound with an amine represented by the following general formula (VI):

(VI)

(in which R represents a hydrogen atom, a hydroxyl group, or a methyl group) to obtain the diene iron complex compound represented by the general formula (I).

[7] The method for producing a sanshool according to [6], in which lithium hydroxide is used as a base in the step of reacting the aldehyde compound with triethyl 4-phosphonocrotonate.

[8] The method for producing a sanshool according to [2] or [3], further including:

a step of reducing a diene iron complex compound represented by the following general formula (III)

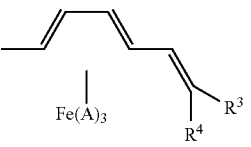
(III)

(in which A represents CO, P(R^A)_3, CN, NO, SO(R^A)_3, or N(R^A)_2; R^A represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group) to an aldehyde compound;

a step of reacting the obtained aldehyde compound with triethyl 4-phosphonocrotonate to obtain a diene iron complex compound represented by the following general formula (VII):

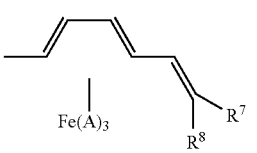
(VII)

(in which A represents CO, P(R^A)_3, CN, NO, SO(R^A)_3, or N(R^A)_2; R^A represents a straight chain or branched chain alkyl group having 1 to 4 carbon atoms or an aryl group having 6 to 12 carbon atoms; and one of $R^7$ and $R^8$ represents a hydrogen atom and the other one thereof represents a structure represented by the following formula (VIII)):

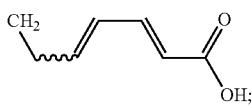

(VIII)

and a step of reacting the obtained diene iron complex compound represented by the general formula (VII) with an amine represented by the following general formula (VI):

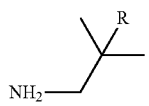

(VI)

(in which R represents a hydrogen atom, a hydroxyl group, or a methyl group) to obtain the diene iron complex compound represented by the general formula (I).

[9] The method for producing a sanshool according to [8], in which lithium hydroxide is used as a base in the step of reacting the aldehyde compound with triethyl 4-phosphonocrotonate.

[10] The method for producing a sanshool according to any one of [4] to [9], further including a step of reacting a compound represented by the following formula (IX):

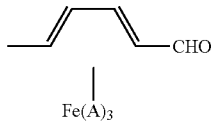

(IX)

with (3-cyanopropyl)triphenylphosphonium salt or 4-(1-phenyl-1H-tetrazole-5-ylsulfonyl)butanenitrile to obtain the diene iron complex compound represented by the general formula (III).

Effects of the Invention

According to the present invention, there can be provided the method for producing a sanshool, which can produce a sanshool in the short process and with high stereoselectivity, as well as the diene iron complex compound that is an intermediate useful for the production method.

MODE FOR CARRYING OUT THE INVENTION

Hereinbelow, embodiments of the present invention will be described in detail.

[Diene Iron Complex Compound]

A diene iron complex compound according to the present invention is represented by the following general formula (I):

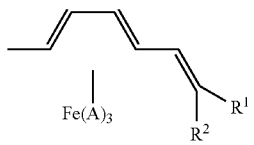

(I)

(in which A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^1$ and $R^2$ represents a hydrogen atom and the other one thereof represents a structure represented by the following formula (II)):

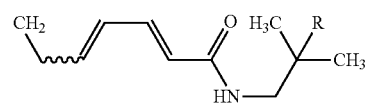

(II)

(in which R represents a hydrogen atom, a hydroxyl group, or a methyl group). In addition, in the formula (II), the wavy line portion represents either a cis (Z) or trans (E) stereoisomer, and preferably a trans isomer, as shown in the following formula (II'). Likewise, the wavy line portions in the formula (V) and the formula (VIII) also represent either a cis (Z) or trans (E) stereoisomer, and preferably a trans isomer.

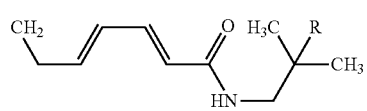

(II')

Examples of the straight chain or branched chain alkyl group having 1 to 4 carbon atoms represented by the $R^A$ include a methyl group, an ethyl group, a propyl group, an isopropyl group, a butyl group, a t-butyl group, and the like, and preferred is a methyl group. Additionally, examples of the aryl group having 6 to 12 carbon atoms include a phenyl group, a 2-pyridyl group, a 3-pyridyl group, a 4-pyridyl group, a 2-thienyl group, a 3-thienyl group, and the like, and preferred is a phenyl group.

By reacting the diene iron complex compound with a deprotecting agent, a sanshool such as a gamma-sanshool, a delta-sanshool, or a hydroxy-gamma-sanshool can be conveniently produced. Examples of the deprotecting agent include cerium (IV) compounds such as cerium ammonium nitrate (CAN), trimethylamine N-oxide, pyridine N-oxide, iron (III) chloride, copper (II) chloride, dichlorodicyano benzoquinone, hydrogen peroxide, and the like, among which cerium (IV) compounds, trimethylamine N-oxide, and pyridine N-oxide are suitable. Most preferable is trimethylamine N-oxide that can produce a sanshool with less by-products.

In addition, sanshools are unstable, and particularly, in gamma-sanshool and delta-sanshool, decomposition (isomerization or the like) occurs markedly under light exposure. However, the diene iron complex compound of the present invention described above is relatively stable and hardly causes isomerization or the like due to light. Therefore, sanshools can be produced by preserving the diene iron complex compound of the present invention and performing deprotection reaction when needed.

[Method for Producing Sanshool]

A method for producing a sanshool according to the present invention is characterized by reacting the diene iron complex compound represented by the general formula (I) with a deprotecting agent. Examples of the deprotecting agent include cerium (IV) compounds such as cerium ammonium nitrate (CAN), trimethylamine N-oxide, pyridine N-oxide, iron (III) chloride, copper (II) chloride, dichlorodicyano benzoquinone, hydrogen peroxide, and the like, among which cerium (IV) compounds, trimethylamine N-oxide, and pyridine N-oxide are suitable, and most preferable is trimethylamine N-oxide that can produce a sanshool with less by-product formation.

The temperature for reaction with the deprotecting agent is not particularly limited, and preferably the reaction is performed at −20 to 50° C. In addition, preferably, the reaction is performed within 1 hour.

The method for producing a sanshool of the present invention preferably includes:

a step (A) of reducing the diene iron complex compound represented by the general formula (III) to an aldehyde compound;

a step (B) of reacting the obtained aldehyde compound with (E)-N-isobutyl-diethylphosphonocrotonic acid amide, (E)-N-(2-methyl-2-hydroxy-propyl)-diethylphosphonocrotonic acid amide, or (E)-N-(2,2-dimethyl-propyl)-diethylphosphonocrotonic acid amide to obtain the diene iron complex compound represented by the general formula (I); and a step of reacting the obtained diene iron complex compound represented by the general formula (I) with a deprotecting agent.

<Step (A)>

An example of the reaction of the above step (A) can be represented by the following formula. The following reaction formula shows a case of using the diene iron complex compound represented by the general formula (III) in which A represents CO and $R^4$ represents a 2-cyanoethyl group.

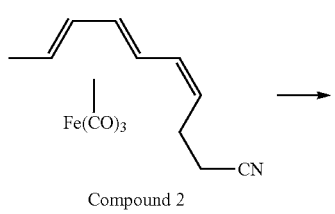

Compound 2

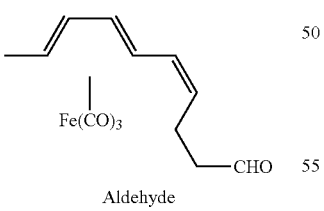

Aldehyde

Examples of a reducing agent include lithium triethoxyaluminium hydride, lithium tri(sec-butyl)borohydride, diisobutylaluminium hydride (DIBAL-H), and the like, among which preferable is DIBAL-H. An example of a suitable reaction format is to perform a reduction reaction using DIBAL-H in an amount of 1.0 to 2.0 equivalents with respect to the diene iron complex compound represented by the general formula (III), while cooling to a temperature of −80 to −20° C. in an organic solvent, such as toluene.

In the diene iron complex compound represented by the general formula (III), for example, when A represents CO in the formula (III), the complex compound can be synthesized by a Wittig reaction or the like from a compound 1 represented by the following formula:

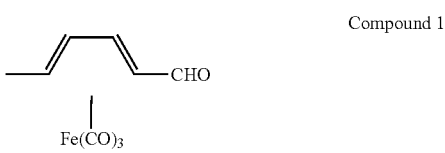

Compound 1

In addition, different geometric isomers may be formed by using different reactions such as a Wittig reaction, a Horner-Wadsworth-Emmons reaction, and a Julia-Lythgoe olefination, as the situation demands.

The Wittig reaction can be performed, for example, with reference to methods described in literature such as Wittig, G; Schollkopf, U. Ber., 1954, 87, 1318, and Maryanoff, B. E. et al. Chem. Rev. 1989, 89, 863.

The Horner-Wadsworth-Emmons reaction can be performed, for example, with reference to methods described in literature such as Horner, L.; Hoffmann, H. M. R.; Wippel, H. G; Klahre, G. Ber., 1959, 92, 2499, Maryanoff, 13. E.; Reitz, A. B. Chem. Rev. 1989, 89, 863, and Kelly, S. E. Comprehensive Organic Synthesis 1991, 1, 729.

The Julia-Lythgoe olefination can be performed, for example, with reference to methods described in literature such as Julia, M; Paris, J. M. Tetrahedron Lett., 1973, 4833, and Blakemore, P. RJCS Perkin Trans., 1, 2002, 2563.

In addition, the above compound 1 can be easily synthesized, for example, by heating and stirring 2,4-hexadienal easily obtainable as a commercially available reagent and an iron complex such as $Fe_3(CO)_{12}$.

<Step (B)>

An example of the reaction of the above step (B) can be represented by the following formula. The following reaction formula shows a case of using the diene iron complex compound represented by the general formula (III) in which A represents CO and $R^4$ represents a 2-cyanoethyl group to react with (E)-N-isobutyl-diethylphosphonocrotonic acid amide.

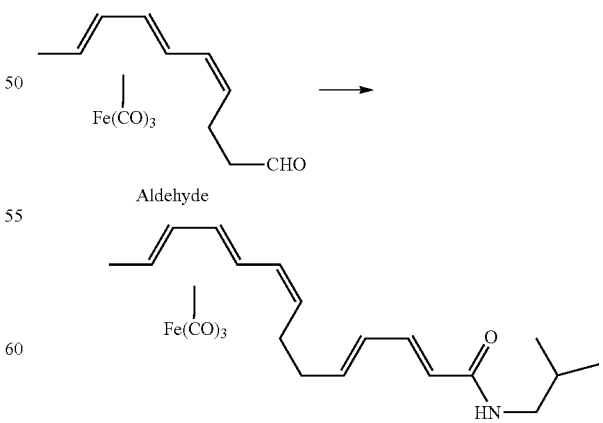

Together with the above compound (tricarbonyl[(10,11,12,13-η)-(2E,4E,8Z,10E,12E)-N-isobutyltetradeca-2,4,8,10,12-pentaenamide]iron), an isomer (3-geo) represented by the following formula may be obtained, but preferably, the amount of the isomer is minimum. The isomer represented by the following formula can be easily separated, for example, by silica gel chromatography. Furthermore, purity of the isomer can be increased by recrystallization of the above compound (tricarbonyl[(10,11,12,13-η)-(2E,4E,8Z,10E,12E)-N-isobutyltetradeca-2,4,8,10,12-pentaenamide]iron). The crystallization preferably uses a solvent of hexane/ether.

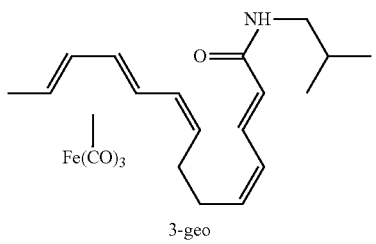

3-geo

The reaction between the above aldehyde and (E)-N-isobutyl-diethylphosphono-crotonic acid amide, (E)-N-(2-methyl-2-hydroxy-propyl)-diethylphosphono-crotonic acid amide, or (E)-N-(2,2-dimethyl-propyl)-diethylphosphono-crotonic acid amide can be accomplished, for example, by an E-selective Horner-Wadsworth-Emmons reaction. Specifically, in an organic solvent such as alcohol, THF, 1,2-dimethoxyethane, or DMSO is dissolved (E)-N-isobutyl-diethylphosphonocrotonic acid amide, (E)-N-(2-methyl-2-hydroxy-propyl)-diethylphosphonocrotonic acid amide, or (E)-N-(2,2-dimethyl-propyl)-diethylphosphonocrotonic acid amide, and the mixed solution is reacted with a base such as sodium hydride, sodium methoxide, potassium carbonate, DBU (diazabicycloundecene), triethylamine, lithium chloride, or NaHMDS (sodium bis(trimethylsilyl)amide) to generate anion. Thereto is added the aldehyde compound obtained above to react for a certain time, preferably for 1 to 8 hours, and more preferably for 1 to 5 hours. Reaction temperature is not particularly limited and can be selected appropriately from −80° C. to a temperature of heating under reflux. The base is preferably lithium chloride due to enhanced stereoselectivity.

(E)-N-isobutyl-diethylphosphonocrotonic acid amide is a compound represented by the following formula:

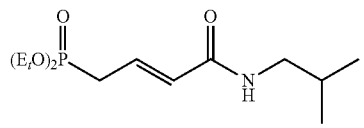

(E)-N-isobutyl-diethylphosphonocrotonic acid amide can be synthesized, for example, using ethyl 4-bromocrotonate as a raw material, which is easily obtainable as a commercially available reagent, by going through a reaction with triethyl phosphite, hydrolysis, and amidation. An example of such a synthetic route can be represented by the following formula. The synthetic route represented by the formula below is as follows: ethyl 4-bromocrotonate is reacted with triethyl phosphite by heating at 130° C. to obtain triethyl 4-phosphonocrotonate; next, the obtained triethyl 4-phosphonocrotonate is hydrolyzed with potassium hydroxide to obtain 4-diethylphosphonocrotonic acid; then, an amidation reaction of the 4-diethylphosphonocrotonic acid with isobutylamine is performed to obtain (E)-N-isobutyl-diethylphosphonocrotonic acid amide.

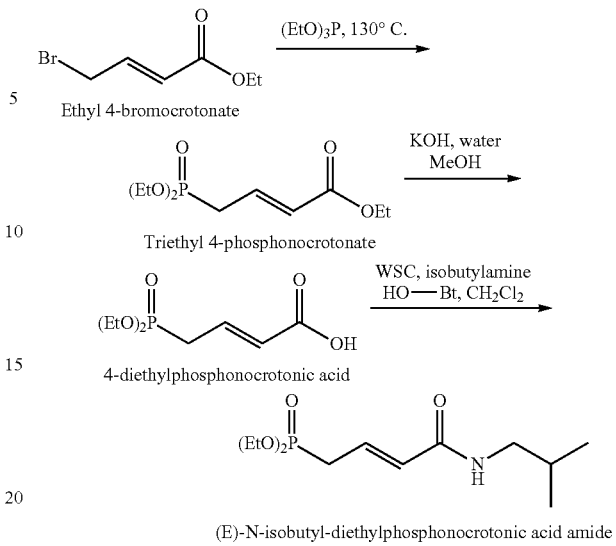

<Step (C)>

The step of reacting the diene iron complex compound represented by the general formula (I) with a deprotecting agent is the same as that described above.

In addition, the method for producing a sanshool of the present invention preferably includes:

a step (A) of reducing the diene iron complex compound represented by the general formula (III) to an aldehyde compound;

a step (D) of reacting the obtained aldehyde compound with triethyl 4-phosphonocrotonate to obtain the diene iron complex compound represented by the general formula (IV);

a step (E) of hydrolyzing the diene iron complex compound represented by the general formula (IV) and then reacting the resulting compound with an amine represented by the general formula (VI) to obtain the diene iron complex compound represented by the general formula (I); and a step (C) of reacting the obtained diene iron complex compound represented by the general formula (I) with a deprotecting agent.

<Step (D)>

The above step (D) is the same as the above step (B) except that triethyl 4-phosphonocrotonate is used without using any of (E)-N-isobutyl-diethylphosphonocrotonic acid amide, (E)-N-(2-methyl-2-hydroxy-propyl)-diethylphosphonocrotonic acid amide, and (E)-N-(2,2-dimethyl-propyl)-diethylphosphonocrotonic acid amide.

<Step (E)>

In the above step (E), first, an ester bond of the diene iron complex compound represented by the general formula (IV) is hydrolyzed. The hydrolysis is not limited to any specific method and may be performed by a known method.

Next, an amidation reaction between a carboxyl group obtained by the hydrolysis and the amine represented by the general formula (VI) is performed to obtain the diene iron complex compound represented by the general formula (I). The amidation reaction can be performed by a common method, but may be performed preferably by a condensation reaction of the amine with N-methyl-2-chloropyridinium iodide or a condensation reaction using a combination of a water-soluble condensing agent such as a water-soluble carbodiimide (e.g. 1-ethyl-3-(3-dimethylaminopropyl)carbodiimide hydrochloride) and hydroxybenzotriazole (HOBt).

In addition, the amine represented by the general formula (VI) can be synthesized by a known method. For example, an amine of the formula (VI) in which R represents a hydroxy group, namely, 2-hydroxy-2-methylpropylamine can be obtained by reacting benzylamine in an amount of 1.1 equivalent with respect to 1,2-epoxy-2-methylpropane (EMP) and then performing deprotection through catalytic hydrogenation reaction. The above reaction can be performed, for example, with reference to a method described in Candice Menzzi-Smarrito et al., J. Agric. Food Chem. 57, 1982 (2009).

In addition, the method for producing a sanshool of the present invention preferably includes:

a step (A) of reducing the diene iron complex compound represented by the general formula (III) to an aldehyde compound;

a step (F) of reacting the obtained aldehyde compound with 4-diethylphosphonocrotonic acid to obtain the diene iron complex compound represented by the general formula (VII);

a step (G) of reacting the obtained diene iron complex compound represented by the general formula (VII) with the amine represented by the general formula (VI) to obtain the diene iron complex compound represented by the general formula (I); and a step (C) of reacting the obtained diene iron complex compound represented by the general formula (I) with a deprotecting agent.

<Step (F)>

The above step (F) is the same as the above step (B) except that 4-diethylphosphonocrotonic acid is used without using any of (E)-N-isobutyl-diethylphosphonocrotonic acid amide, (E)-N-(2-methyl-2-hydroxy-propyl)-diethylphosphonocrotonic acid amide, and (E)-N-(2,2-dimethyl-propyl)-diethylphosphonocrotonic acid amide.

<Step (G)>

The above step (G) can be performed in the same manner as the amidation reaction in the above step (E).

Additionally, the method for producing a sanshool of the present invention preferably further includes, in addition to the above-described steps, a step (H) of reacting a compound represented by the following formula (IX):

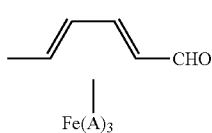

(IX)

with 3-cyanopropyl triphenylphosphonium salt or 4-(1-phenyl-1H-tetrazole-5-ylsulfonyl)butanenitrile to obtain the diene iron complex compound represented by the general formula (III).

<Step (H)>

In the diene iron complex compound represented by the general formula (III), for example, when A represents CO in the formula (III), the complex compound can be synthesized from the compound 1 represented by the following formula:

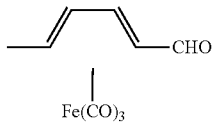

Compound 1 by a Witting reaction using 3-cyanopropyl triphenylphosphonium salt or a Julia-Kocienski olefination reaction using 4-(1-phenyl-1H-tetrazole-5-ylsulfonyl)butanenitrile. The Julia-Kocienski olefination reaction can be performed, for example, with reference to a method described in literature such as P. J. Kocienski, et al., Synlett, 1998, 26. The Wittig reaction allows, among diene iron complex compounds represented by the general formula (III), the selective synthesis of a diene iron complex compound in which $R^4$ represents a 2-cyanoethyl group.

In addition, with the Julia-Kocienski olefination reaction, among the diene iron complex compounds represented by the general formula (III), a diene iron complex compound in which $R^3$ represents a 2-cyanoethyl group (that is, one having an E, E, E-triene skeleton) can be selectively synthesized.

After that, using the obtained diene iron complex compound represented by the general formula (III), by going through the above-described steps (A), (B), (C), (D), (E), (F), and (G) according to need, a delta-sanshool can be produced.

EXAMPLES

Experiment Example 1

Synthesis of tricarbonyl[(2,3,4,5-η)-(2E,4E)-hexa-2,4-dienal]iron

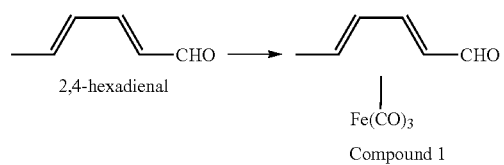

Compound 1

2,4-Hexadienal (1.81 mL) was added to a suspension of $Fe_3(CO)_{12}$ (5.7 g) in toluene (30 mL) at room temperature, and the mixture was stirred at 60° C. for 24 hours. Then, the reaction mixture was stirred at 80° C. for 1 hour. The reaction mixture was purified by silica gel chromatography (hexane→hexane/ethyl acetate=10:1) to give 2.84 g (a yield of 70.8%) of tricarbonyl[2,3,4,5-η]-(2E,4E)-hexa-2,4-dienal]iron as yellow oil.

Data of the obtained compound are as follows:

$^1$H-NMR (CDCl$_3$, 400 MHz) δ: 1.26 (1H, dd, J=4.4, 8.3 Hz), 1.51 (3H, d, J=6.1 Hz), 1.70 (1H, dq, J=8.7, 6.1 Hz), 5.30 (1H, dd, J=5.1, 8.7 Hz), 5.77 (1H, dd, J=5.1, 8.3 Hz), 9.26 (1H, d, J=4.4 Hz);

ESI-LRMS: m/z: +ESI 259 [M+Na]$^+$, 237 [M+H]$^+$, −ESI 235 [M−H]$^-$;

ESI-HRMS: m/z: 258.9666 (Calcd for C$_9$H$_8$O$_4$FeNa: 258.9670).

Experiment Example 2-1

Synthesis of tricarbonyl[(6,7,8,9-η)-(4Z,6E,8E)-deca-4,6,8-trienenitrile]iron

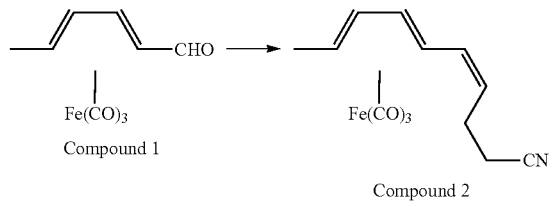

Compound 1 → Compound 2

1) To a mixture of 3-cyanopropyl(triphenyl)phosphonium bromide (PPh$_3$P$^+$(CH$_2$)$_3$CN Br$^-$) (12.3 g, 30.0 mol) in THF (30 mL) at 0° C. under argon atmosphere was added a suspension of sodium hexamethyldisilazide (NaHMDS) (1.0 mol/L) in THF (30 mL). The obtained red-orange colored solution was stirred at the same temperature for 30 minutes. After stopping the stirring, the resulting solution was allowed to stand at room temperature for approximately 1 hour until NaBr was completely precipitated to be separated, thereby obtaining the ylide solution.

2) To a solution of tricarbonyl[(2,3,4,5-η)-(2E,4E)-hexa-2,4-dienal]iron (4.20 g) in THF (35 mL) was added dropwise 0.5 mol/L solution (60.0 mL) of the ylide at −78° C. under argon atmosphere. Then, the reaction solution was stirred at −78° C. for 1 hour. While gradually warming the reaction solution to −20° C., the solution was stirred for 1.5 hours. The resulting reaction solution was quenched with saturated ammonium chloride aqueous solution, and the water layer was extracted with ethyl acetate. The combined organic layer was washed with brine and dried over anhydrous sodium sulfate. The organic solvent was concentrated under reduced pressure, and the residue was purified by silica gel chromatography (hexane/ethyl acetate=5:1) to give 4.61 g (a yield of 90.4%) of tricarbonyl[(6,7,8,9-η)-(4Z,6E,8E)-deca-4,6,8-trienenitrile]iron as an yellow solid.

Data of the obtained compound are as follows:

$^1$H-NMR (CDCl$_3$, 400 MHz) δ: 1.42-1.45 (4H, m), 1.75 (1H, dd, J=9.6, 10.7 Hz), 2.36-2.47 (4H, m), 5.07 (1H, dd, J=4.9, 7.3 Hz), 5.19 (1H, dd, J=4.9, 8.2 Hz), 5.32 (1H, td, J=7.3, 10.7 Hz), 5.54 (1H, t, J=10.7 Hz);

$^{13}$C-NMR (CDCl$_3$, 100 MHz) δ: 17.05, 19.18, 23.83, 54.48, 57.60, 82.40, 85.97, 119.13, 125.14, 134.15, 212.05;

ESI-MS m/z: +ESI 310 [M+Na]$^+$, 288 [M+H]$^+$, −ESI 286 [M−H]$^-$;

HRESI-MS m/z: 310.0143 (Calcd for C$_{13}$H$_{13}$NO$_3$FeNa: 310.0143);

IR (KBr): cm$^{-1}$: 2033, 1952, 625, 568.

Experiment Examples 2-2 to 2-5

Reaction was performed in the same manner as the above Experiment Example 2-1 except that the base, the solvent, and the temperature to be used were changed to those shown in Table 1 below. Table 1 below shows yields of tricarbonyl [(6,7,8,9-η)-(4Z,6E,8E)-deca-4,6,8-trienenitrile] iron.

TABLE 1

|  | Base (solvent) | Temperature of 1) | Solvent of 2) | Temperature of 2) | Yield (%) |
| --- | --- | --- | --- | --- | --- |
| Experiment Example 2-1 | NaHMDS (THF) | 0° C.→r.t. | THF | −78° C.→−20° C. | 90.4 |
| Experiment Example 2-2 | n-BuLi, HMPA (THF) | 0° C. | THF | −78° C.→0° C. | 27.9 |
| Experiment Example 2-3 | t-BuOK (DMSO-THF) | r.t. | THF | −20° C. | 17.1 |
| Experiment Example 2-4 | NaH (DMSO-THF) | 0° C. | THF | 0° C. | 54.7 |
| Experiment Example 2-5 | NaH (DMSO) | r.t. | DMSO | r.t. | 20.6 |

Experiment Example 3-1

Synthesis of triethyl 4-phosphonocrotonate

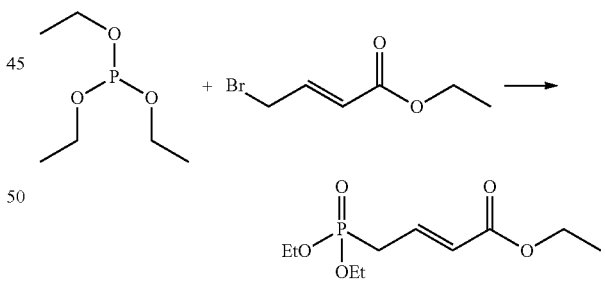

Ethyl 4-bromocrotonate (7.0 mL) was added to triethylphosphite (9.9 mL) at 120 to 130° C. during 60 minutes periods. After the generation of ethyl bromide ceased, the reaction solution was stirred at the same temperature for 3 hours. After cooling, the resulting reaction solution was concentrated under reduced pressure. Then the residue was purified by distillation at 150 to 210° C. under reduced pressure (17 to 21 hPa) to give triethyl 4-phosphonocrotonate as colorless oil.

Data of the obtained compound are as follows:
$^1$H-NMR (CDCl$_3$, 400 MHz) δ: 1.27-1.35 (9H, t×3), 2.74 (2H, dd, J=7.8, 22.9 Hz), 4.08-4.22 (6H, m), 5.96 (1H, ddd, J=1.4, 4.8, 13.8 Hz), 6.88 (1H, td, J=7.8, 22.9 Hz).

Experiment Example 3-2

Synthesis of 4-diethylphosphonocrotonic acid

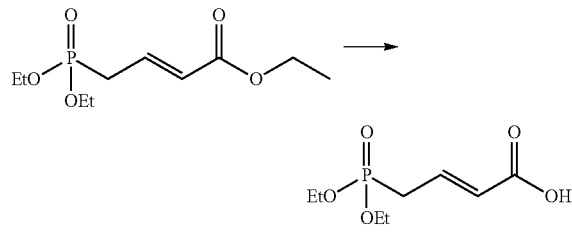

To a solution of triethyl 4-phosphonocrotonate (5.53 g) in water (36 mL) was added a solution of potassium hydroxide (1.69 g) in water (36 mL) at room temperature, and the reaction solution was stirred for 3 hours. The resulting reaction solution was washed with dichloromethane, and the water layer was acidified to pH2 with concentrated hydrochloric acid and extracted with dichloromethane (550 mL). The combined organic layer was dried over anhydrous magnesium sulfate and concentrated to dryness under reduced pressure to give 4.41 g of 4-diethylphosphonocrotonic acid as a colorless solid.

Data of the obtained compound are as follows:
Melting Point: 73.0-75.0° C., $^1$H-NMR (CDCl$_3$, 400 MHz) δ: 1.33 (6H, t, J=7.1 Hz), 2.79 (2H, dd, J=8.0, 23.0 Hz), 4.11-4.18 (4H, m), 5.97 (1H, dd, J=5.1, 15.5 Hz), 6.94 (1H, td, J=7.8, 23.0 Hz).

Experiment Example 3-3

Synthesis of (E)-N-isobutyl-diethylphosphonocrotonic acid amide

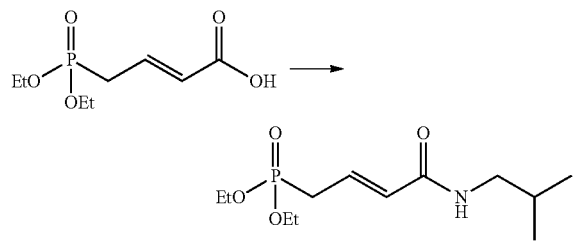

A solution of 4-diethylphosphonocrotonic acid (5.0 g), 1-ethyl-3-(3-dimethylaminopropyl)carbodiimide hydrochloride (5.2 g) and HO-Bt (hydroxybenzotriazole) (4.6 g) in dichloromethane (36.5 g) was stirred for 5 minutes under argon atmosphere. To the above reaction solution was added isobutylamine (4.9 mL), and the reaction solution was stirred at room temperature for 6 hours. A saturated sodium carbonate aqueous solution was added to the resulting reaction solution, and the water layer was extracted with dichloromethane. The combined organic layer was dried over anhydrous sodium sulfate. The organic solvent was concentrated under reduced pressure, and the residue was purified by silica gel chromatography (ethyl acetat→ethyl acetate/methanol=10/1) to give (E)-N-isobutyl-diethylphosphonocrotonic acid amide as colorless viscous oil.

Data of the obtained compound are as follows:
$^1$H-NMR (CDCl$_3$, 400 MHz) δ: 0.92 (6H, d, J=6.8 Hz), 1.32 (6H, t, J=7.1 Hz), 1.80 (1H, m), 2.72 (2H, dd, J=7.8, 23.3 Hz), 3.15 (2H, t, J=6.6 Hz), 4.08-4.16 (4H, m), 5.55 (1H, brs), 5.97 (1H, dd, J=4.9, 15.0 Hz), 6.74 (1H, td, J=7.8, 23.3 Hz); $^{13}$C-NMR (CDCl$_3$, 100 MHz), δ: 164.9 (d, J=2.5 Hz), 132.6 (d, J=10.7 Hz), 128.4 (d, J=13.2 Hz), 62.2 (d, J=6.6 Hz), 46.9 (s), 30.1 (d, J=139.8 Hz), 28.5 (s), 20.1 (s), 16.4 (d, J=5.8 Hz); ESI-MS m/z: +ESI 278 [M+H]$^+$−ESI 276 [M−H]$^-$; HRESI-MS m/z: 355.0250 (Calcd for C$_{12}$H$_{25}$O$_4$NP: 278.1513); IR (film): cm$^{-1}$: 3476, 3288, 1677, 1628, 1554, 1244, 1023.

Experiment Example 4-1

Synthesis of tricarbonyl[(10,11,12,13-η)-(2E,4E,8Z,10E,12E)-N-isobutyltetradeca-2,4,8,10,12-pentaenamide]iron

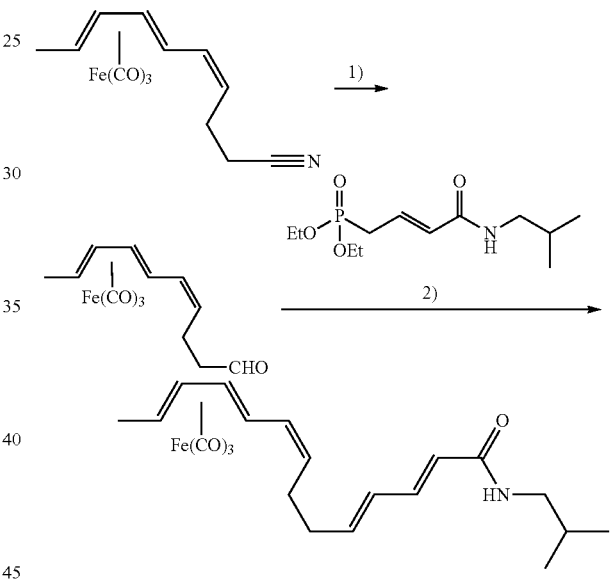

1) To a solution of Tricarbonyl[(6,7,8,9-η)-(4Z,6E,8E)-deca-4,6,8-trienenitrile]iron (100.2 mg) in toluene (2.5 mL) at −20° C. under argon atmosphere was added dropwise DIBAL-H (0.52 mL). Then the reaction solution was stirred at −20° C. for 1 hour. The reaction solution was quenched with 1 mol/L hydrochloric acid, and the mixed solution was stirred for 5 minutes. Then, the water layer was extracted with ethyl acetate. The combined organic layer was washed with brine and dried over anhydrous sodium sulfate. The organic solvent was concentrated under reduced pressure to give an aldehyde compound.

2) To a solution of (E)-N-isobutyl-diethylphosphonocrotonic acid amide (126.5 mg) in THF (tetrahydrofuran) (2 mL) under argon atmosphere was added a 1 mol/L solution of NaHMDS ((sodium bis(trimethylsilyl)amide) in THF (0.5 mL) at −20° C., and the mixed solution was stirred at −20° C. for 15 minutes and at room temperature for 10 minutes. To the mixed solution was added a solution of the above aldehyde in THF (1.0 mL) at −20° C. Subsequently, the reaction solution was stirred while warming from −20 to 0° C. during 4 hours. Then, the resulting reaction solution was quenched with 1 mol/L hydrochloric acid, and the water layer was extracted with ethyl acetate. The combined organic layer was washed with a saturated aqueous solution of sodium carbonate and brine and dried over sodium sulfate. The organic solvent was concentrated under reduced pressure, and the residue was purified by silica gel chromatography (ethyl acetate/hexane=4/1) to give tricarbonyl[(10,11,12,13-η)-(2E,4E,8Z,10E,12E)-N-isobutyltetradeca-2,4,8,10,12-penta enamide] iron (27.6 mg). In addition, the following isomer 3-geo (51.4 mg) was also obtained.

Both of the products were recrystallized from hexane/diethylether to give yellow solids.

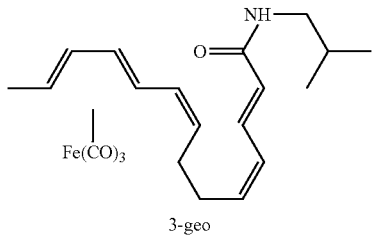

3-geo

Data of the obtained compound are as follows: Tricarbonyl [(10,11,12,13-η)-(2E,4E,8Z,10E,12E)-N-isobutyltetradeca-2,4,8,10,12-pentaenamide]iron:

Melting Point 73.5-75.5° C. (hexane/Et$_2$O), $^1$H-NMR (CDCl$_3$, 400 MHz) δ: 0.92 (6H, d, J=6.8 Hz), 1.36 (1H, m), 1.42 (3H, d, J=5.8 Hz), 1.75-1.85 (1H, m), 1.88 (1H, dd, J=8.7, 10.5 Hz), 2.21-2.27 (4H, m), 3.17 (2H, t, J=6.5 Hz), 5.03 (1H, dd, J=5.1, 8.2 Hz), 5.14 (1H, dd, J=5.1, 8.7 Hz), 5.30 (1H, td, J=6.3, 10.5 Hz), 5.41 (1H, t, J=10.5 Hz), 5.49 (1H, brs), 5.77 (1H, d, J=15.1 Hz), 6.05 (1H, td, J=6.3, 15.1 Hz), 6.16 (1H, dd, J=10.7, 15.1 Hz), 7.19 (1H, dd, J=10.7, 15.1 Hz); $^{13}$C-NMR (CDCl$_3$, 100 MHz) δ: 212.37, 166.23, 141.57, 140.98, 131.49, 129.57, 128.85, 122.26, 85.47, 82.23, 57.08, 56.24, 46.91, 32.41, 28.62, 27.15, 20.10, 19.17; ESI-MS m/z: +ESI 436 [M+Na]$^+$, 414 [M+H]$^+$, −ESI 412 [M−H]$^−$. HRESI-MS m/z: 414.1357 (Calcd for C$_{21}$H$_{28}$NO$_4$Fe: 414.1362); IR (film): cm$^{-1}$: 3290, 2037, 1966.

Isomer: $^1$H-NMR (CDCl$_3$, 400 MHz) δ: 0.93 (6H, d, J=6.87 Hz), 1.33 (1H, m), 1.42 (3H, d, J=5.8 Hz), 1.81 (1H, m), 1.88 (1H, dd, J=9.6 Hz), 2.22 (2H, dd, J=7.1, 14.0 Hz), 2.41 (2H, dd, J=7.4, 14.0 Hz), 3.18 (2H, t, J=6.7 Hz), 5.03 (1H, dd, J=4.9, 7.8 Hz), 5.14 (1H, dd, J=4.9, 9.6 Hz), 5.32 (1H, td, J=7.1, 10.7 Hz), 5.41 (1H, dd, J=9.6, 10.7 Hz), 5.49 (1H, brs), 5.77 (1H, td, J=7.8, 10.6 Hz), 5.84 (1H, d, J=14.7 Hz), 6.12 (1H, dd, J=10.6, 11.5 Hz), 7.52 (1H, dd, J=11.5, 14.7 Hz); ESI-MS m/z: +ESI 436 [M+Na]$^+$, 414 [M+H]$^+$, −ESI 412 [M−H]$^−$. HRESI-MS m/z: 414.1357 (Calcd for C$_{21}$H$_{28}$NO$_4$Fe: 414.1362).

Experiment Example 4-2

Synthesis of tricarbonyl[(10,11,12,13-η)-(2E,4E,8Z,10E,12E)-N-isobutyltetradeca-2,4,8,10,12-pentaenamide]iron

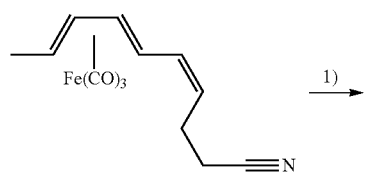

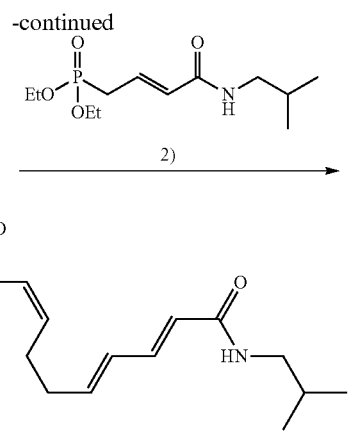

1) To a solution of tricarbonyl [(6,7,8,9-η)-(4Z,6E,8E)-deca-4,6,8-trienenitrile]iron (1.02 g) in toluene (25 mL) was added dropwise DIBAL-H (0.52 mL) at −20° C. under argon atmosphere. The reaction solution was stirred at −20° C. for 1 hour. The reaction solution was quenched with 1 mol/L hydrochloric acid, and the mixed solution was stirred for 15 minutes. Then, the water layer was extracted with ethyl acetate. The combined organic layer was washed with brine and dried over anhydrous sodium sulfate. The organic solvent was concentrated under reduced pressure to obtain an aldehyde compound.

2) A suspension of (E)-N-isobutyl-diethylphosphonocrotonic acid amide (1.96 g), MS4A (molecular sieves 4A) (5.61 g), and lithium hydroxide (609.9 mg) in THF (20 mL) was stirred at room temperature for 1.5 hours. Then a solution of the above aldehyde in THF (10 mL) was added to the reaction, and the reaction solution was refluxed for 2 hours.

After cooling, the reaction solution was filtered through a silica gel column eluting with ethyl acetate, followed by concentration under reduced pressure, thereby obtaining a crude product. The crude product was purified by silica gel chromatography (ethyl acetate/hexane=5/1→2/1) to give desired product (825.9 mg) as a light yellow solid.

Experiment Examples 4-3 to 4-7

Reaction was performed in the same manner as the Experiment Example 4-2, except that, in the 2) above, the base and temperature to be used were changed to those shown in Table 2 below. Table 2 below shows yields of the isomer 3-geo (designated as 3 g) and tricarbonyl[(10,11,12,13-η)-(2E,4E,8Z,10E,12E)-N-isobutyltetradeca-2,4,8,10,12-pentaenamide]iron (designated as 3). In Table 2, A represents tricarbonyl[(6,7,8,9-η)-(4Z,6E,8E)-deca-4,6,8-trienenitrile]iron.

TABLE 2

| | Reaction conditions | Yield (%) |
|---|---|---|
| Experiment Example 4-1 | A (1.3 eq), NaHMDS (1.4 eq), THF, −20° C. to r.t., 4 h | 3 g (36%) 3 (19%) |
| Experiment Example 4-2 | A (2.0 eq), LiOH (4.0 eq), MS4A, THF, reflux, 2.0 h | 3 (56%) |
| Experiment Example 4-3 | A (2.0 eq), LiOH (4.0 eq), MS4A, THF, reflux, 2.0 h | 3 (57%) |
| Experiment Example 4-4 | A (1.3 eq), LiOH (1.4 eq), MS4A, THF, reflux, 4.5 h | 3 (51%) |
| Experiment Example 4-5 | A (1.3 eq), LiOH (1.5 eq), MS4A, THF, reflux, 12 h | 3 (40%) |
| Experiment Example 4-6 | A (2.0 eq), LiOH (4.0 eq), MS4A, THF, reflux, 2.0 h | 3 (54%) |

TABLE 2-continued

| | Reaction conditions | Yield (%) |
|---|---|---|
| Experiment Example 4-7 | A (2.0 eq), LiOH (4.0 eq), MS4A, DBU (1.0 eq), THF, reflux, 2.0 h | 3 (54%) |

Experiment Example 5-1

Synthesis of (2E,4E,8Z,10E,12E)-N-isobutyltetradeca-2,4,8,10,12-pentaenamide

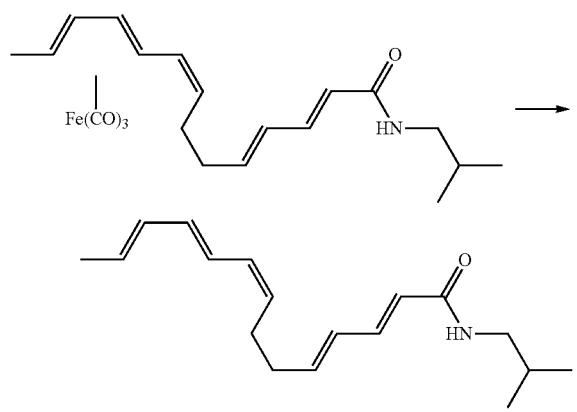

A mixture of tricarbonyl[(10,11,12,13-η)-(2E,4E,8Z,10E,12E)-N-isobutyltetradeca-2,4,8,10,12-pentaenamide]iron (39.8 mg) and trimethylamine-N-oxide (150.8 mg) in acetonitrile (1.0 mL) at room temperature under a nitrogen atmosphere was stirred for 1 hour. The reaction solution was purified by silica gel chromatography (ethyl acetate/hexane=1/1) to give a desired product as a colorless solid (20.6 mg).

Data of the obtained compound are as follows:

$^1$H-NMR (CDCl$_3$, 400 MHz) δ: 0.92 (6H, d, J=6.7 Hz), 1.78 (3H, d, J=7.7 Hz), 1.79 (1H, m), 2.24 (2H, dd, J=7.5, 14.0 Hz), 2.32 (2H, dd, J=7.0, 14.8 Hz), 3.17 (2H, t, J=6.7 Hz), 5.37 (1H, td, J=7.5, 10.4 Hz), 5.49 (1H, brs), 5.72 (1H, td, J=7.0, 13.4 Hz), 5.76 (1H, d, J=15.0 Hz), 5.99-6.21 (5H, m), 6.33 (1H, dd, J=11.3, 13.4 Hz), 7.18 (1H, dd, J=11.3, 15.0 Hz).

Experiment Example 5-2

Synthesis of (2E,4Z,8Z,10E,12E)-N-isobutyltetradeca-2,4,8,10,12-pentaenamide

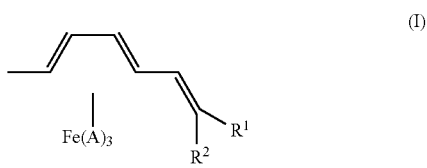

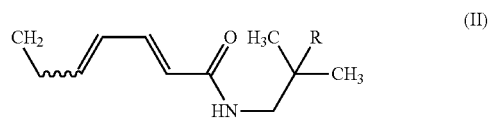

A mixture of the above isomer 3-geo (42.8 mg) and trimethylamine-N-oxide (75.1 mg) in acetonitrile (1.0 mL) at room temperature under a nitrogen atmosphere was stirred for 1 hour. To the mixed solution was added trimethylamine-N-oxide (86.8 mg), and the mixed solution was stirred for 10 minutes. The reaction solution was purified by silica gel chromatography (ethyl acetate/hexane=1/1) to give a desired product as a colorless solid (24.0 mg).

Data of the obtained compound are as follows:

$^1$H-NMR (CDCl$_3$, 400 MHz) δ: 0.93 (6H, d, J=6.5 Hz), 1.78 (3H, d, J=6.8 Hz), 1.81 (1H, m), 2.24 (2H, dd, J=7.3, 14.6 Hz), 2.41 (2H, dd, J=7.3, 14.6 Hz), 3.18 (2H, t, J=6.5 Hz), 5.37 (1H, td, J=7.3, 10.9 Hz), 5.49 (1H, brs), 5.69-5.81 (2H, m), 5.83 (1H, t, J=14.9 Hz), 6.02 (1H, d, J=10.9 Hz), 6.08-6.20 (3H, m), 6.34 (1H, dd, J=10.9, 12.6 Hz), 7.53 (1H, dd, J=12.6, 14.9 Hz).

The invention claimed is:

1. A diene iron complex compound represented by the following general formula (I):

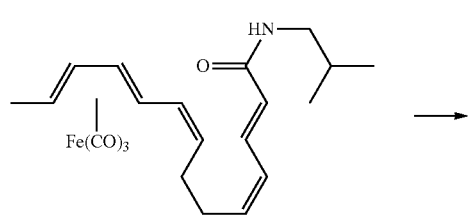

(wherein A represents CO, P(R$^A$)$_3$, CN, NO, SO(R$^A$)$_3$, or N(R$^A$)$_2$; R$^A$ represents a straight chain or branched chain alkyl group having 1 to 4 carbon atoms or an aryl group having 6 to 12 carbon atoms; and one of R$^1$ and R$^2$ represents a hydrogen atom and the other one thereof represents a structure represented by the following formula (II)):

(II)

$$\text{CH}_2 \diagdown \diagup \diagdown \diagup \diagdown \overset{O}{\underset{HN}{\diagdown}} \overset{H_3C}{\underset{CH_3}{\diagdown}} R$$

(wherein R represents a hydrogen atom, a hydroxyl group, or a methyl group).

2. A method for producing a sanshool, comprising a step of reacting a diene iron complex compound represented by the following general formula (I):

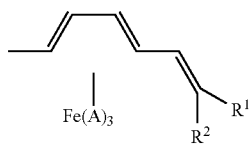

(I)

(wherein A represents CO, P($R^A$)$_3$, CN, NO, SO($R^A$)$_3$, or N($R^A$)$_2$; $R^A$ represents a straight chain or branched chain alkyl group having 1 to 4 carbon atoms or an aryl group having 6 to 12 carbon atoms; and one of $R^1$ and $R^2$ represents a hydrogen atom and the other one thereof represents a structure represented by the following formula (II)):

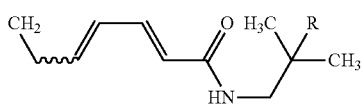

(II)

(wherein R represents a hydrogen atom, a hydroxyl group, or a methyl group) with a deprotecting agent.

3. The method for producing a sanshool according to claim 2, wherein the deprotecting agent is selected from the group consisting of cerium (IV) compounds, trimethylamine N-oxide, pyridine N-oxide, iron (III) chloride, copper (II) chloride, dichlorodicyano benzoquinone, and hydrogen peroxide.

4. The method for producing a sanshool according to claim 2, further comprising:
a step of reducing a diene iron complex compound represented by the following general formula (III):

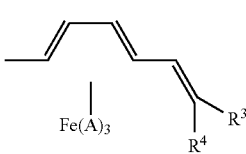

(III)

(wherein A represents CO, P($R^A$)$_3$, CN, NO, SO($R^A$)$_3$, or N($R^A$)$_2$; $R^A$ represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group) to an aldehyde compound; and
a step of reacting the obtained aldehyde compound with (E)-N-isobutyl-diethylphosphonocrotonic acid amide, (E)-N-(2-methyl-2-hydroxy-propyl)-diethylphosphonocrotonic acid amide, or (E)-N-(2,2-dimethyl-propyl)-diethylphosphonocrotonic acid amide to obtain the diene iron complex compound represented by the general formula (I).

5. The method for producing a sanshool according to claim 4, wherein lithium hydroxide is used as a base in the step of reacting the aldehyde compound with (E)-N-isobutyl-diethylphosphonocrotonic acid amide, (E)-N-(2-methyl-2-hydroxy-propyl)-diethylphosphonocrotonic acid amide, or (E)-N-(2,2-dimethyl-propyl)-diethylphosphonocrotonic acid amide.

6. The method for producing a sanshool according to claim 2, further comprising:
a step of reducing a diene iron complex compound represented by the following general formula (III)

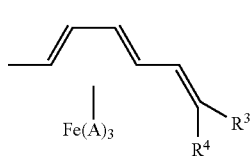

(III)

(wherein A represents CO, P($R^A$)$_3$, CN, NO, SO($R^A$)$_3$, or N($R^A$)$_2$; $R^A$ represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group) to an aldehyde compound;
a step of reacting the obtained aldehyde compound with triethyl 4-phosphonocrotonate to obtain a diene iron complex compound represented by the following general formula (IV):

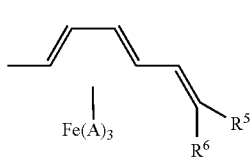

(IV)

(wherein A represents CO, P($R^A$)$_3$, CN, NO, SO($R^A$)$_3$, or N($R^A$)$_2$; $R^A$ represents a straight chain or branched chain alkyl group having 1 to 4 carbon atoms or an aryl group having 6 to 12 carbon atoms; and one of $R^5$ and $R^6$ represents a hydrogen atom and the other one thereof represents a structure represented by the following formula (V)),

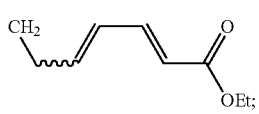

(V)

and
a step of hydrolyzing the obtained diene iron complex compound represented by the general formula (IV) and then reacting the resulting compound with an amine represented by the following general formula (VI):

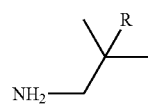

(VI)

(wherein R represents a hydrogen atom, a hydroxyl group, or a methyl group) to obtain the diene iron complex compound represented by the general formula (I).

7. The method for producing a sanshool according to claim 6, wherein lithium hydroxide is used as a base in the step of reacting the aldehyde compound with triethyl 4-phosphonocrotonate.

8. The method for producing a sanshool according to claim 2, further comprising:

a step of reducing a diene iron complex compound represented by the following general formula (III)

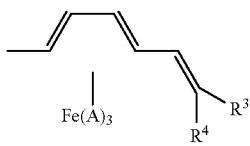
(III)

(wherein A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^3$ and $R^4$ represents a hydrogen atom and the other one thereof represents a 2-cyanoethyl group) to an aldehyde compound;

a step of reacting the obtained aldehyde compound with triethyl 4-phosphonocrotonate to obtain a diene iron complex compound represented by the following general formula (VII):

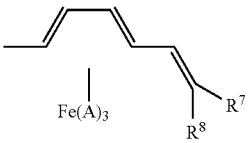
(VII)

(wherein A represents CO, $P(R^A)_3$, CN, NO, $SO(R^A)_3$, or $N(R^A)_2$; $R^A$ represents a straight chain or branched chain alkyl group having 1 to 4 carbon atoms or an aryl group having 6 to 12 carbon atoms; and one of $R^7$ and $R^8$ represents a hydrogen atom and the other one thereof represents a structure represented by the following formula (VIII)):

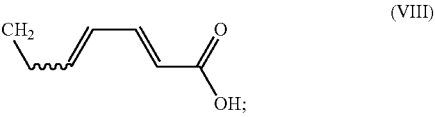
(VIII)

and a step of reacting the obtained diene iron complex compound represented by the general formula (VII) with an amine represented by the following general formula (VI):

(VI)

(wherein R represents a hydrogen atom, a hydroxyl group, or a methyl group) to obtain the diene iron complex compound represented by the general formula (I).

9. The method for producing a sanshool according to claim 8, wherein lithium hydroxide is used as a base in the step of reacting the aldehyde compound with triethyl 4-phosphonocrotonate.

10. The method for producing a sanshool according to claim 4, further comprising a step of reacting a compound represented by the following formula (IX):

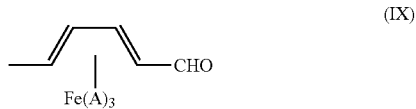
(IX)

with (3-cyanopropyl)triphenylphosphonium salt or 4-(1-phenyl-1H-tetrazole-5-ylsulfonyl)butanenitrile to obtain the diene iron complex compound represented by the general formula (III).

* * * * *